United States Patent [19]

Zabotto et al.

[11] Patent Number: 5,165,917
[45] Date of Patent: Nov. 24, 1992

[54] EYE MAKEUP REMOVER WITH TWO SEPARATE PHASES

[75] Inventors: Arlette Zabotto, Paris; Jean-Claude Contamin, Chilly Mazarin; Nathalie Plaisant, L'Hay Les Roses, all of France

[73] Assignee: Societe Anonyme dite: L'Oreal, France

[21] Appl. No.: 634,080

[22] Filed: Dec. 26, 1990

Related U.S. Application Data

[63] Continuation-in-part of Ser. No. 433,992, Nov. 9, 1989, abandoned.

[30] Foreign Application Priority Data

Nov. 9, 1988 [FR] France .................. 88 14641

[51] Int. Cl.⁵ .................. A61K 7/06; A61K 7/00
[52] U.S. Cl. .................. 424/70; 424/401; 514/938; 514/846
[58] Field of Search .................. 424/62, 170; 514/772, 514/785, 789, 846, 937, 938; 252/DIG. 5

[56] References Cited

U.S. PATENT DOCUMENTS

| | | | |
|---|---|---|---|
| 3,533,955 | 10/1970 | Pader et al. | 252/153 |
| 4,323,468 | 4/1982 | Grollier et al. | 252/174.17 |
| 4,543,205 | 9/1985 | Contamin | 252/546 |
| 4,661,343 | 4/1987 | Zabotto et al. | 424/59 |
| 4,673,526 | 6/1987 | Zabotto et al. | 252/174.17 |
| 4,715,982 | 12/1987 | Zabotto et al. | 252/106 |
| 4,732,692 | 3/1988 | Zabotto et al. | 252/174.17 |

FOREIGN PATENT DOCUMENTS 951213 7/1974 Canada.

OTHER PUBLICATIONS

Abstract, vol. 12, No. 306 (Aug. 19, 1988) Japan 63-79808 (Sep. 4, 1988).
Abstract of France 2,254,636 issued Jul. 1975.

Primary Examiner—Thurman K. Page
Assistant Examiner—Sally Gardner
Attorney, Agent, or Firm—Oliff & Berridge

[57] ABSTRACT

A composition suitable for effective and comfortable removal of both waterproof and non-waterproof eye makeup is disclosed which includes an aqueous phase containing at least one surfactant and an oily phase containing at least one cosmetic oil. The surfactant concentration may be up to 3 wt % of the total weight of the composition. The weight ratio of the aqueous phase and the oily phase may be from 30:70 to 60:40.

14 Claims, No Drawings

EYE MAKEUP REMOVER WITH TWO SEPARATE PHASES

This is a continuation-in-part of application Ser. No. 07/433,992, filed Nov. 9, 1989 now abandoned.

BACKGROUND OF THE INVENTION

The present invention eye makeup remover comprising two separate phases: an aqueous phase and an oily phase.

Eye makeup comprises application to the eyelids and eyelashes, of a composition containing colored pigments, which composition may or may not be oil-based; eye shadow is used for the eyelids and mascara for the eyelashes.

Oil-based makeup products are generally designated "waterproof" (WP) while those not containing oil are designated "non-waterproof" (NWP).

Removal of the first type of makeup (WP) is generally performed with the aid of a makeup remover based on oil, particularly vaseline oil which may be mixed with fatty esters. These makeup removal products are, of course, able to remove makeup of the second type (NWP) but are so unpleasant to apply that, when they are not indispensable, it is preferable to use a classical cleansing lotion.

These lotions, which contain an aqueous solution of a surfactant, usually allow for makeup of the NWP type to be properly removed but have the disadvantage of drying the skin by removing its natural oil film.

As a result of the foregoing, the appropriate makeup remover should be employed, depending on the type of makeup used. However, whatever the type of makeup used, it is particularly difficult to combine good removal of the makeup with good cosmetic characteristics such as pleasantness and comfort during and after application.

An object of the present invention is to provide a solution to the problem of removing makeup from the eyes by offering, for the first time, a composition able to remove makeup of both the WP and NWP types in a particularly effective manner and under extremely satisfactory conditions as far as cosmetic properties are concerned.

Another object of the invention is to avoid any feeling of tightening or irritation upon application and to confer on the skin both coolness and mildness by forming an oil film that reconstitutes the natural oil film of the skin.

SUMMARY OF THE INVENTION

The present invention relates to a cosmetic composition suitable for removal of both waterproof eye makeup and nonwaterproof eye makeup, comprising an aqueous phase containing at least one surfactant and an oily phase having at least one cosmetic oil.

DETAILED DESCRIPTION OF THE PREFERRED EMBODIMENTS

These and other objects are achieved by the present invention, which includes a cosmetic composition for the eyes, non-foaming and usable for removing makeup of the waterproof and non-waterproof types, comprising two separate phases: a lower or aqueous phase containing at least one surfactant and an upper or oily phase containing at least one cosmetic oil, with the weight ratio between the lower and upper phases ranging from 30:70 to 60:40, and the surfactant being present in amount up to 3% by weight.

The comparative studies that have been performed and are reported below show a synergistic effect between the two phases as far as both the makeup removal properties and the cosmetic properties are concerned.

The aqueous phase may be composed of sterile demineralized water or a floral water such as rosewater, cornflower [Centaurea] water, chamomile water, or linden water.

The surfactant, which can be of the anionic, nonionic, or amphoteric type, but preferably of the nonionic type, is preferably present in the aqueous phase in a proportion between 0.005 and 3 wt. % (of active material) and more preferably between 0.1 and 1.5 wt. % with respect to the total weight of the makeup removal composition.

Particularly preferred nonionic surfactants include:
fatty esters of polyoxyethylene sorbitol, such as the product sold as "TWEEN 20" by the Atlas Company;
fatty polyoxyethylene alcohols, such as the product sold as "REMCOPAL 21912 AL" by the Gerland Company;
polyoxyethylene alkylphenols, such as the product sold as "TRITON X 100" by the Rohm and Haas Company; and
ethylene oxide and propylene oxide condensates, such as those sold under the name "SYNPERONIC PE" by the ICI Company and in particular those referenced L 31, L 64, F 38, F 88, L 92, F 103, F 108, and F 127.

Anionic surfactants which are useful in the present invention include:
alkyl ether sulfates, such as the product sold under the name "TEXAPON ASV" by the Henkel Company,
alkyl sulfoacetates, such as the product sold under the name "LATHANOL LAL" by the Stepan Company,
alkyl sulfosuccinates, such as the product sold under the name "Sodium Dioctyl Sulfosuccinate" by the Rhone Poulenc Company,
alkylamidosulfosuccinates, such as the product sold under the name "REWODERM S 1333" by the Rewo Company,
alkylamidopolypeptides, such as the product sold under the name "LAMEPON S" by the Grunau Company, and
acylsarcosinates, such as the product sold under the name "ORAMIX L 30" by the Seppic Company.

Amphoteric surfactants which are useful in the present invention include
alkylamidopropyl dimethylbetaines, such as the product sold under the name "TEGO BETAINE L 7" by the Goldschmidt company,
alkylamidobetaines, such as the product sold under the name "INCRONAM 30" by the Croda Company,
imidazoline derivatives, such as the product sold under the name "CHIMEXANE HD" by the Chimex Company, and
N-alkyl beta-imino-dipropionates, such as the product sold under the name "MONATERIC ISA 35" by the Mona Company.

The oily phase of the makeup removal composition according to the invention comprises a mixture of oils which can be mineral, vegetable, or synthetic oils or silicone oils. Mineral oils which are particularly useful in the present invention include vaseline oil and higher aliphatic hydrocarbons, such as, for example, isohexadecane. Particularly useful vegetable oils include jojoba oil and safflower oil. Particularly useful silicone oils include cyclopentadimethylsiloxane sold under the name "VOLATIL SILICONE 7158" by the Union Carbide Company. Particularly useful synthetic oils include alkyl palmitates having 2 to 10 carbon atoms, such as isopropyl palmitate or 2-ethylhexyl palmitate, and alkyl adipates with 2 to 10 carbon atoms, such as di(2-ethylhexyl) adipate.

In one particular embodiment of the invention, the oily phase contains at least one alkyl palmitate having 2 to 10 carbon atoms in a proportion of at least 8% and preferably between 10 and 30% with respect to the total weight of the makeup removal composition.

In a preferred embodiment of the invention, the oily phase contains at least one silicone oil in a proportion of at least 8% and preferably between 15 and 50% with respect to the total weight of the makeup removal composition.

The makeup removal composition according to the invention may also contain conventional cosmetic adjuvants which may be in either phase according to whether they are hydrophilic or lipophilic, such as for example perfumes, preservatives, dyes, softening agents, a buffer, moisteners, and possibly an electrolyte such as sodium chloride to provide isotonicity in the aqueous phase.

Moisteners having utility in the present invention include hexylene glycol and polyethylene glycol 600, being present in a concentration of less than or equal to 5%, preferably between 0.05 and 2%.

Softening agents useful in the present invention include allantoin and certain plant extracts.

EXAMPLES

The following Examples disclose illustrative, specific eye makeup removal compositions according to the present invention. The specific embodiments are disclosed for illustrative purposes only, and are not intended to limit the generic scope of the invention in any manner whatsoever.

EXAMPLE 1

A two-phase makeup removal composition according to the invention is obtained by packing, in a flask, 50% of an oily phase (A) and 50% of an aqueous phase (B) containing the following ingredients:

|  | % |
|---|---|
| A. Oily Phase | |
| 2-ethylhexyl palmitate | 20 |
| di(2-ethylhexyl)adipate | 20 |
| cyclopentadimethylsiloxane | 60 |
| B. Aqueous Phase | |
| oxyethylated sorbitan laurate with 20 moles of ethylene oxide | 0.5 |
| hexylene glycol | 0.5 |
| monopotassium phosphate | 0.1 |
| dipotassium phosphate | 0.3 |
| sodium chloride | 0.9 |
| perfumes | qs |
| dyes | qs |
| preservatives | qs |
| demineralized water, to: | qsp 100 |

EXAMPLE 2

A two-phase makeup removal composition according to the invention is obtained by packing, in a flask, 50% of an oily phase (A) and 50% of an aqueous phase (B) containing the following ingredients:

|  | % |
|---|---|
| A. Oily Phase | |
| isopropyl palmitate | 40 |
| jojoba oil | 2 |
| cyclopentadimethylsiloxane | 58 |
| B. Aqueous Phase | |
| condensate of ethylene oxide and propylene oxide sold by the ICI Company under the name "Synperonic PE/F38" | 2 |
| propylene glycol | 0.4 |
| triethanolamine | 0.08 |
| sodium chloride | 0.8 |
| perfumes | qs |
| preservatives | qs |
| dyes | qs |
| demineralized water. to: | qsp 100 |

EXAMPLE 3

A two-phase makeup removal composition according to the invention is obtained by packing, in a flask, 70% of an oily phase (A) and 30% of an aqueous phase (B) containing the following ingredients:

|  | % |
|---|---|
| A. Oily Phase | |
| vaseline oil | 25 |
| 2-ethylhexyl palmitate | 25 |
| cyclopentadimethylsiloxane | 50 |
| B. Aqueous Phase | |
| 1-hydroxyethyl-2-lauryl-3-carboxymethylimidazolinium betaine | 2 |
| allantoin | 0.15 |
| triethanolamine | 0.04 |
| perfumes | qs |
| preservatives | qs |
| dyes | qs |
| demineralized water. to: | qsp 100 |

EXAMPLE 4

A two-phase makeup removal composition according to the invention is obtained by packing, in a flask, 50% of an oily phase (A) and 60% of an aqueous phase (B) containing the following ingredients:

|  | % |
|---|---|
| A. Oily Phase | |
| 2-ethylhexyl palmitate | 50 |
| di(2-ethylhexyl)adipate | 50 |
| B. Aqueous Phase | |
| ricinoleic monoethanolamide monosulfosuccinate | 0.5 |
| hexylene glycol | 0.5 |
| monopotassium phosphate | 0.1 |
| dipotassium phosphate | 0.3 |
| sodium chloride | 0.9 |
| perfumes | qs |
| preservatives | qs |
| dyes | qs |
| demineralized water, to: | qsp 100 |

EXAMPLE 5

A two-phase makeup removal composition according to the invention is obtained by packing, in a flask, 50% of an oily phase (A) and 50% of an aqueous phase (B) containing the following ingredients:

|  | % |
|---|---|
| A. Oily Phase | |
| cyclopentadimethylsiloxane | 59.75 |
| isohexadecane | 40.00 |
| benzyl alcohol | 0.25 |
| B. Aqueous Phase | |
| condensate of ethylene oxide and propylene oxide sold by the ICI Company under the name "Synperonic PE/F38" | 0.5 |
| monopotassium phosphate | 0.1 |
| dipotassium phosphate | 0.3 |
| sodium chloride | 0.9 |
| hexylene glycol | 0.5 |
| preservatives | qs |
| perfume | qs |
| water, to: | qsp 100 |

EXAMPLE 6

A two-phase makeup removal composition according to the invention is obtained by packing, in a flask, 45% of an oily phase (A) and 55% of an aqueous phase (B) containing the following ingredients:

|  | % |
|---|---|
| A. Oily phase | |
| 2-ethylhexyl palmitate | 25 |
| isohexadecane | 25 |
| cyclopentadimethylsiloxane | 50 |
| B - Aqueous phase | |
| condensate of ethylene oxide and propylene oxide (MW 12.000) sold by the ICI Company under the name "Poloxamer" | 0.04 |
| hexylene glycol | 0.3 |
| monopotassium phosphate | 0.1 |
| dipotassium phosphate | 0.3 |
| sodium chloride | 1.2 |
| perfume | qs |
| preservatives | qs |
| dyes | qs |
| demineralized water, to: | qsp 100 |

EXAMPLE 7

A two-phase makeup removal composition according to the invention is obtained by packing, in a flask, 50% of an oily phase (A) and 50% of an aqueous phase (B) containing the following ingredients:

|  | % |
|---|---|
| A - Oily phase | |
| di (2-ethylhexyl) adipate | 10 |
| isohexadecane | 40 |
| cyclopentadimethylsiloxane | 49.8 |
| benzyl alcohol | 0.2 |
| B - Aqueous phase | |
| condensate of ethylene oxide and propylene oxide sold by the ICI Company under the name "Poloxamer 338" | 0.02 |
| hexylene glycol | 0.5 |
| sodium chloride | 0.9 |
| monopotassium phosphate | 0.1 |
| dipotassium phosphate | 0.7 |
| perfume | 0.1 |
| preservatives | qs |
| demineralized water, to | qsp 100 |

COMPARATIVE STUDIES

In order to demonstrate the eye makeup removal properties and the good cosmetic properties of the compositions according to the invention, the following makeup removal products were compared:

MAKEUP REMOVAL PRODUCT A: This makeup removal product corresponds to that of Example 1 as described above.

MAKEUP REMOVAL PRODUCT B: Aqueous cleansing lotion with the following composition:

|  | % |
|---|---|
| oxyethylated sorbitan laurate with 20 moles of ethylene oxide | 0.5 |
| hexylene glycol | 0.5 |
| monopotassium phosphate | 0.1 |
| dipotassium phosphate | 0.3 |
| sodium chloride | 0.9 |
| perfumes | qs |
| preservatives | qs |
| dyes | qs |
| demineralized water, to: | qsp 100 |

This composition corresponds to the aqueous phase of the makeup removal product in Example 1 above.

MAKEUP REMOVAL PRODUCT C: Cleansing oil with the following composition:

|  | % |
|---|---|
| 2-ethylhexyl palmitate | 20 |
| di(2-ethylhexyl)adipate | 20 |
| cyclopentadimethylsiloxane | 60 |

This oil corresponds to the oily phase of the makeup removal product in Example 1 above.

MAKEUP REMOVAL PRODUCT D: Two-phase makeup-removal with the following composition:

(A) 50% of an oily phase with the following composition:

|  | % |
|---|---|
| 2-ethylhexyl palmitate | 20 |
| di(2-ethylhexyl)adipate | 20 |
| cyclopentadimethylsiloxane | 60 | and (B) 50% water.

The oily phase of this composition corresponds to that of Example 1 above.

Five groups, each consisting of 17 women were formed. Each group was given:

Group 1: a NWP mascara and a bottle of makeup removal products A and B;

Group 2: a NWP mascara and a bottle of makeup removal products A and C;

Group 3: a NWP mascara and a bottle of makeup removal products A and D;

Group 4: a WP mascara and a bottle of makeup removal products A and C;

Group 5: a WP mascara and a bottle of makeup removal products A and D.

Each woman was ask to make up her eyelashes with the mascara provided to her, each day for a week, and to remove the makeup in the evening using makeup removal product A according to the invention for the right eye and the comparison makeup removal product for the left eye.

After this period, the impressions of the users were collected and tabulated in Tables I and I below:

TABLE I

| NWP Mascara | | | Makeup Removal Compositions | | | |
|---|---|---|---|---|---|---|
| | | | A* | B | C | D |
| Makeup Removal Properties | GOOD | | 16 | 3 | 13 | 8 |
| | POOR | | 1 | 14 | 4 | 9 |
| Cosmetic Properties | freshness | good | 13 | 17 | 3 | 8 |
| | | inadequate | 4 | 0 | 14 | 9 |
| | mildness | good | 17 | 17 | 9 | 5 |
| | | poor | 0 | 0 | 8 | 12 |
| | final appearance of skin | natural oil film | 14 | 0 | 17 | 14 |
| | | nothing to report | 3 | 17 | 0 | 3 |
| disadvantages | tingling | | 0 | 0 | 0 | 0 |
| | awkwardness | | 0 | 0 | 3 | 3 |
| | discomfort | | 2.5 | 0 | 6 | 6 |
| | nothing to report | | 14.5 | 17 | 8 | 8 |

*Mean value of three groups who used an NWP mascara

TABLE II

| WP Mascara | | | Makeup Removal Compositions | | |
|---|---|---|---|---|---|
| | | | A* | C | D |
| Makeup Removal Properties | GOOD | | 15 | 15 | 2 |
| | POOR | | 2 | 2 | 15 |
| Cosmetic Properties | freshness | good | 13 | 2 | 8 |
| | | inadequate | 4 | 15 | 9 |
| | mildness | good | 17 | 8 | 5 |
| | | poor | 0 | 9 | 12 |
| | final appearance of skin | natural oil film | 14 | 17 | 14 |
| | | nothing to report | 3 | 0 | 3 |
| disadvantages | tingling | | 0 | 0 | 0 |
| | awkwardness | | 1 | 3 | 4 |
| | discomfort | | 3 | 6 | 6 |
| | nothing to report | | 13 | 8 | 7 |

*Mean value of both groups who used a WP mascara.

As can be seen from Table I, makeup removal product A according to the invention combines good makeup removal properties with good cosmetic properties as far as the NWP mascara is concerned, which is not the case for the other makeup removal products. A comparison with makeup removal product D shows the importance of the presence of a surfactant in the aqueous phase of the makeup removal product according to the invention.

Table II shows that although the removal properties of product A according to the invention for a WP mascara are comparable to those of product C, the cosmetic properties are distinctly superior, particularly in terms of the freshness and mildness furnished by the aqueous phase containing a surfactant of the makeup removal product according to the invention, during and after use.

We claim:

1. A non-foaming cosmetic composition suitable for removal of both waterproof eye makeup and non-waterproof eye makeup comprising two separate phases, a lower aqueous phase comprising at least one surfactant selected from the group consisting of anionic surfactants, nonionic surfactants and amphoteric surfactants, and an upper oily phase comprising at least one cosmetic oil, the weight ratio of said aqueous phase to said oily phase being in the range of from 30:70 to 60:40, said surfactant being present in a surfactant effective amount up to 3 weight percent with respect to the total weight of the composition.

2. The composition of claim 1 wherein said aqueous phase is selected from the group consisting of sterile demineralized water, rose water, cornflower water, chamomile water, and linden water.

3. The composition of claim 1, wherein said surfactant is present in a concentration of from 0.005 to 3 weight percent with respect to the total weight of the composition.

4. The composition of claim 1 wherein said surfactant is present in a concentration of from 0.1 to 1.5 weight percent with respect to the total weight of the composition.

5. The composition of claim 1, wherein said oil is selected from the group consisting of vaseline oil, isohexadecane, jojoba oil, safflower oil, silicone oil, and synthetic oil.

6. The composition of claim 5, wherein said synthetic oil is an alkyl palmitate or an alkyl adipate, wherein said alkyl radical has from 2 to 10 carbon atoms.

7. The composition of claim 1, wherein said oily phase contains at least one alkyl palmitate having from 2 to 10 carbon atoms in a proportion of at least 8 wt. % with respect to the total weight of the composition.

8. The composition of claim 7, wherein said oily phase comprises from 10 to 30% of an alkyl palmitate having from 2 to 10 carbon atoms with respect to the total weight of the composition.

9. The composition of claim 7, wherein said alkyl palmitate is isopropyl palmitate or 2-ethylhexyl palmitate.

10. The composition of claim 1, wherein said oily phase contains at least one silicone oil in a proportion of at least 8% with respect to the total weight of the composition.

11. The composition of claim 1, further comprising, in at least one of said two separate phases, at least one cosmetic additive selective from the group consisting of a perfume, a preservative, a dye, a softener, a buffer, a moistener, and an electrolyte.

12. The composition of claim 2, wherein said surfactant is a nonionic surfactant.

13. The composition of claim 10, wherein said silicone oil is present in a concentration of from 15 to 50% with respect to the total weight of the composition.

14. The composition of claim 11, wherein said electrolyte is sodium chloride.

* * * * *

REEXAMINATION CERTIFICATE (4012th)

United States Patent [19]
Zabotto et al.

[11] B1 5,165,917
[45] Certificate Issued Mar. 14, 2000

[54] EYE MAKEUP REMOVER WITH TWO SEPARATE PHASES

[75] Inventors: Arlette Zabotto, Paris; Jean-Claude Contamin, Chilly Mazarin; Nathalie Plaisant, L'Hay les Roses, all of France

[73] Assignee: Societe Anonyme Dite: L'Oreal, Paris, France

Reexamination Request:
No. 90/005,051, Jul. 31, 1998

Reexamination Certificate for:
Patent No.: 5,165,917
Issued: Nov. 24, 1992
Appl. No.: 07/634,080
Filed: Dec. 26, 1990

Related U.S. Application Data

[63] Continuation-in-part of application No. 07/433,992, Nov. 9, 1989, abandoned.

[30]  Foreign Application Priority Data

Nov. 9, 1988 [FR] France .................................... 88 14641

[51] Int. Cl.$^7$ ............................... A61K 7/02; A61K 7/00; A61K 7/06
[52] U.S. Cl. ...................... 424/70.12; 510/130; 510/136; 510/137; 514/938; 514/846; 424/70.21; 424/70.22; 424/70.27; 424/70.31; 424/401
[58] Field of Search ............................... 424/70.12, 70.1, 424/401, 70.11; 510/130, 136, 137; 514/938, 846

[56]   References Cited

FOREIGN PATENT DOCUMENTS 3627313   8/1986   Germany .
55-139312  10/1980  Japan .

*Primary Examiner*—Sally Gardner

[57]   ABSTRACT

A composition suitable for effective and comfortable removal of both waterproof and non-waterproof eye makeup is disclosed which includes an aqueous phase containing at least one surfactant and an oily phase containing at least one cosmetic oil. The surfactant concentration may be up to 3 wt % of the total weight of the composition. The weight ratio of the aqueous phase and the oily phase may be from 30:70 to 60:40.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is cancelled.

Claims 2–5, 7–8, 10 and 11 are determined to be patentable as amended.

Claims 6, 9 and 12–14, dependent on an amended claim, are determined to be patentable.

New claims 15–122 are added and determined to be patentable.

2. The composition of claim [1] *10,* wherein said aqueous phase is selected from the group consisting of sterile demineralized water, rose water, cornflower water, chamomile water, and linden water.

3. The composition of claim [1] *10,* wherein said surfactant is present in a concentration of from 0.005 to 3 weight percent with respect to the total weight of the composition.

4. The composition of claim [1] *10* wherein said surfactant is present in a concentration of from 0.1 to 1.5 weight percent with respect to the total weight of the composition.

5. The composition of claim [1] *10,* wherein said oil [is] *further comprises at least one member* selected from the group consisting of vaseline oil, isohexedecane, jojoba oil, safflower oil, [silicone oil,] and synthetic oil.

7. The composition of claim [1] *10,* wherein said oily phase [contains] *further comprises* at least one alkyl palmitate having from 2 to 10 carbon atoms in a proportion of at least 8 wt. % with respect to the total weight of the composition.

8. The composition of claim 7, wherein said oily phase *further* comprises from 10 to 30% of an alkyl palmitate having from 2 to 10 carbon atoms with respect to the total weight of the composition.

10. [The composition of claim 1.] *A non-foaming cosmetic composition suitable for removal of both waterproof eye makeup and non-waterproof eye makeup comprising two separate phases, a lower aqueous phase comprising at least one surfactant selected from the group consisting of anionic surfactants, nonionic surfactants and amphoteric surfactants, and an upper oily phase comprising at least one cosmetic oil, the weight ratio of said aqueous phase to said oily phase being in the range of from 30:70 to 60:40, said surfactant being present in a surfactant effective amount up to 3 weight percent with respect to the total weight of the composition wherein said oily phase contains at least one silicone oil in a proportion of at least 8% with respect to the total weight of the composition.*

11. The composition of claim [1] *10,* further comprising, in at least one of said two separate phases, at least one cosmetic additive selective from the group consisting of a perfume, a preservative, a dye, a softener, a buffer, a moistener, and an electrolyte.

*15. The composition of claim 10, wherein said oily phase further comprises a mineral oil.*

*16. The composition of claim 15, wherein said mineral oil is a higher aliphatic hydrocarbon.*

*17. The composition of claim 16, wherein said higher aliphatic hydrocarbon is isohexadecane.*

*18. The composition of claim 10, further comprising a moistener.*

*19. The composition of claim 18, wherein said moistener is hexylene glycol.*

*20. The composition of claim 10, further comprising an electrolyte.*

*21. The composition of claim 20, wherein said electrolyte is sodium chloride.*

*22. The composition of claim 10, wherein said surfactant comprises a nonionic surfactant.*

*23. The composition of claim 10, wherein said aqueous phase comprises sterile demineralized water.*

*24. The composition of claim 10,*
   *wherein said oily phase further comprises a mineral oil,*
   *further comprising a moistener, and*
   *further comprising an electrolyte.*

*25. The composition of claim 24, wherein said mineral oil is a higher aliphatic hydrocarbon.*

*26. The composition of claim 25, wherein said surfactant comprises a nonionic surfactant.*

*27. The composition of claim 25, wherein said higher aliphatic hydrocarbon is isohexadecane.*

*28. The composition of claim 26, wherein said higher aliphatic hydrocarbon is isohexadecane.*

*29. The composition of claim 27, wherein the electrolyte is sodium chloride.*

*30. The composition of claim 28, wherein the electrolyte is sodium chloride.*

*31. The composition of claim 10,*
   *wherein said oily phase further comprises a mineral oil, and*
   *wherein said surfactant comprises a nonionic surfactant.*

*32. The composition of claim 31, wherein said mineral oil is a higher aliphatic hydrocarbon.*

*33. The composition of claim 32, wherein said mineral oil is isohexadecane.*

*34. The composition of claim 10, wherein said silicone oil comprises cyclopentadimethylsiloxane.*

*35. The composition of claim 24, wherein said silicone oil comprises cyclopentadimethylsiloxane.*

*36. The composition of claim 31, wherein said silicone oil comprises cyclopentadimethylsiloxane.*

*37. A non-foaming cosmetic composition suitable for removal of both waterproof eye makeup and non-waterproof eye makeup comprising two separate phases, a lower aqueous phase comprising at least one surfactant selected from the group consisting of anionic surfactants, nonionic surfactants and amphoteric surfactants, and an upper oily phase comprising at least one cosmetic oil, the weight ratio of said aqueous phase to said oily phase being in the range from 30:70 to 60:40, said surfactant being present in a surfactant effective amount up to 3 weight percent with respect to the total weight of the composition,*
   *wherein said oily phase contains at least one silicone oil in a concentration from 8 to 50% with respect to the total weight of the composition.*

*38. The composition of claim 37, wherein said surfactant is present in a concentration of from 0.005 to 3 weight percent with respect to the total weight of the composition.*

*39. The composition of claim 37, wherein said surfactant is present in a concentration of from 0.1 to 1.5 weight percent with respect to the total weight of the composition.*

40. The composition of claim 37, wherein said surfactant comprises a nonionic surfactant.

41. The composition of claim 37, wherein said oil further comprises at least one member selected from the group consisting of mineral oils, vegetable oils, and synthetic oils.

42. The composition of claim 41, wherein said oil further comprises a mineral oil.

43. The composition of claim 42, wherein said mineral oil is a higher aliphatic hydrocarbon.

44. The composition of claim 43, wherein said higher aliphatic hydrocarbon is isohexadecane.

45. The composition of claim 37, further comprising a moistener.

46. The composition of claim 45, wherein said moistener is hexylene glycol.

47. The composition of claim 37, further comprising an electrolyte.

48. The composition of claim 47, wherein said electrolyte is sodium chloride.

49. The composition of claim 37, wherein said aqueous phase comprises sterile demineralized water.

50. The composition of claim 37,
wherein said oily phase further comprises a mineral oil,
further comprising a moistener, and
further comprising an electrolyte.

51. The composition of claim 50, wherein said mineral oil is a higher aliphatic hydrocarbon.

52. The composition of claim 50, wherein said surfactant comprises a nonionic surfactant.

53. The composition of claim 51, wherein said higher aliphatic hydrocarbon is isohexadecane.

54. The composition of claim 52, wherein said mineral oil is isohexadecane.

55. The composition of claim 53, wherein the electrolyte is sodium chloride.

56. The composition of claim 54, wherein the electrolyte is sodium chloride.

57. The composition of claim 37,
wherein said oily phase further comprises a mineral oil, and
wherein said surfactant comprises a nonionic surfactant.

58. The composition of claim 57, wherein said mineral oil is a higher aliphatic hydrocarbon.

59. The composition of claim 58, wherein said mineral oil is isohexadecane.

60. The composition of claim 37, wherein said silicone oil comprises cyclopentadimethylsiloxane.

61. The composition of claim 50, wherein said silicone oil comprises cyclopentadimethylsiloxane.

62. The composition of claim 57, wherein said silicone oil comprises cyclopentadimethylsiloxane.

63. A non-foaming cosmetic composition suitable for removal of both waterproof eye makeup and non-waterproof eye makeup comprising two separate phases, a lower aqueous phase comprising at least one surfactant selected from the group consisting of anionic surfactants, nonionic surfactants and amphoteric surfactants, and an upper oily phase comprising at least one cosmetic oil, the weight ratio of said aqueous phase to said oily phase being in the range of from 30:70 to 60:40, said surfactant being present in a surfactant effective amount up to 3 weight percent with respect to the total weight of the composition,
wherein said oily phase contains cyclopentadimethylsiloxane.

64. The composition of claim 63, wherein said surfactant is present in a concentration of from 0.005 to 3 weight percent with respect to the total weight of the composition.

65. The composition of claim 63, wherein said surfactant is present in a concentration of from 0.1 to 1.5 weight percent with respect to the total weight of the composition.

66. The composition of claim 63, wherein said surfactant comprises a nonionic surfactant.

67. The composition of claim 63, wherein said oil further comprises at least one member selected from the group consisting of mineral oils, vegetable oils, and synthetic oils.

68. The composition of claim 67, wherein said oil further comprises a mineral oil.

69. The composition of claim 68, wherein said mineral oil is a higher aliphatic hydrocarbon.

70. The composition of claim 69, wherein said higher aliphatic hydrocarbon is isohexadecane.

71. The composition of claim 63, further comprising a moistener.

72. The composition of claim 71, wherein said moistener is hexylene glycol.

73. The composition of claim 63, further comprising an electrolyte.

74. The composition of claim 73, wherein said electrolyte is sodium chloride.

75. The composition of claim 63, wherein said aqueous phase comprises sterile demineralized water.

76. The composition of claim 63,
wherein said oily phase further comprises a mineral oil,
further comprising a moistener, and
further comprising an electrolyte.

77. The composition of claim 76, wherein said mineral oil is a higher aliphatic hydrocarbon.

78. The composition of claim 76, wherein said surfactant comprises a nonionic surfactant.

79. The composition of claim 77, wherein said higher aliphatic hydrocarbon is isohexadecane.

80. The composition of claim 78, wherein said mineral oil is isohexadecane.

81. The composition of claim 79, wherein the electrolyte is sodium chloride.

82. The composition of claim 80, wherein the electrolyte is sodium chloride.

83. The composition of claim 63,
wherein said oily phase further comprises a mineral oil, and
wherein said surfactant comprises a nonionic surfactant.

84. The composition of claim 83, wherein said mineral oil is a higher aliphatic hydrocarbon.

85. The composition of claim 84, wherein said mineral oil is isohexadecane.

86. The composition of claim 63, comprising up to 60% by weight of said cyclopentadimethylsiloxane based on the total weight of the composition.

87. The composition of claim 86, comprising at least 8% by weight of said cyclopentadimethylsiloxane based on the total weight of the composition.

88. The composition of claim 63, comprising at least 8% by weight of said cyclopentadimethylsiloxane based on the total weight of the composition.

89. The composition of claim 63, comprising 15 to 50% by weight of said cyclopentadimethylsiloxane based on the total weight of the composition.

90. The composition of claim 76, comprising up to 60% by weight of said cyclopentadimethylsiloxane based on the total weight of the composition.

91. The composition of claim 90, comprising at least 8% by weight of said cyclopentadimethylsiloxane based on the total weight of the composition.

92. The composition of claim 76, comprising at least 8% by weight of said cyclopentadimethylsiloxane based on the total weight of the composition.

93. The composition of claim 76, comprising 15 to 50% by weight of said cyclopentadimethylsiloxane based on the total weight of the composition.

94. The composition of claim 83, comprising up to 60% by weight of said cyclopentadimethylsiloxane based on the total weight of the composition.

95. The composition of claim 94, comprising at least 8% by weight of said cyclopentadimethylsiloxane based on the total weight of the composition.

96. The composition of claim 83, comprising at least 8% by weight of said cyclopentadimethylsiloxane based on the total weight of the composition.

97. The composition of claim 83, comprising 15 to 50% by weight of said cyclopentadimethylsiloxane based on the total weight of the composition.

98. A non-foaming cosmetic composition suitable for removal of both waterproof eye makeup and non-waterproof eye makeup comprising two separate phases, a lower aqueous phase comprising at least one surfactant selected from the group consisting of anionic surfactants, nonionic surfactants and amphoteric surfactants, and an upper oily phase comprising at least one cosmetic oil, the weight ratio of said aqueous phase to said oily phase being in the range of from 30:70 to 60:40, said surfactant being present in a surfactant effective amount up to 3 weight percent with respect to the total weight of the composition, wherein said oily phase contains isohexadecane.

99. The composition of claim 98, wherein said surfactant is present in a concentration of from 0.005 to 3 weight percent with respect to the total weight of the composition.

100. The composition of claim 98, wherein said surfactant is present in a concentration of from 0.1 to 1.5 weight percent with respect to the total weight of the composition.

101. The composition of claim 98, wherein said surfactant comprises a nonionic surfactant.

102. The composition of claim 98, wherein said oil further comprises at least one member selected from the group consisting of synthetic oils, vegetable oils and silicone oils.

103. The composition of claim 102, wherein said oil further comprises a synthetic oil.

104. The composition of claim 103, wherein said synthetic oil is an alkyl palmitate having 2 to 10 carbon atoms.

105. The composition of claim 104, which contains at least 8% by weight of said alkyl palmitate, with respect to the total weight of the composition.

106. The composition of claim 104, which contains between 10 and 30% by weight of said alkyl palmitate, with respect to the total weight of the composition.

107. The composition of claim 102, wherein said oil further comprises a vegetable oil.

108. The composition of claim 107, wherein said vegetable oil is jojoba oil or safflower oil.

109. The composition of claim 102, wherein said oil further comprises a silicone oil.

110. The composition of claim 109, which contains at least 8% by weight of said silicone oil, with respect to the total weight of the composition.

111. The composition of claim 109, which contains between 15 and 50% by weight of said silicone oil, with respect to the total weight of the composition.

112. The composition of claim 109, wherein said silicone oil is cyclopentadimethylsiloxane.

113. The composition of claim 110, wherein said silicone oil is cyclopentadimethylsiloxane.

114. The composition of claim 111, wherein said silicone oil is cyclopentadimethylsiloxane.

115. The composition of claim 98, further comprising a moistener.

116. The composition of claim 115, wherein said moistener is hexylene glycol.

117. The composition of claim 98, further comprising an electrolyte.

118. The composition of claim 117, wherein said electrolyte is sodium chloride.

119. The composition of claim 98, wherein said aqueous phase comprises sterile demineralized water.

120. The composition of claim 98, further comprising a moistener and an electrolyte.

121. The composition of claim 120, wherein said moistener is hexylene glycol and said electrolyte is sodium chloride.

122. The composition of claim 120, wherein said oil further comprises at least one member selected from the group consisting of synthetic oils, vegetable oils and silicone oils.

\* \* \* \* \*